(12) United States Patent
Hartwich et al.

(10) Patent No.: US 12,186,744 B2
(45) Date of Patent: Jan. 7, 2025

(54) MICROFLUIDIC CARTRIDGE FOR DETECTING BIOMOLECULES

(71) Applicant: FRIZ Biochem GmbH, Neuried (DE)

(72) Inventors: Gerhard Hartwich, Munich (DE); Norbert Persike, Munich (DE); Philip Johnsen, Munich (DE)

(73) Assignee: FRIZ Biochem GmbH, Neuried (DE)

(*) Notice: Subject to any disclaimer, the term of this patent is extended or adjusted under 35 U.S.C. 154(b) by 660 days.

(21) Appl. No.: 15/552,256

(22) PCT Filed: Feb. 16, 2016

(86) PCT No.: PCT/EP2016/000259
§ 371 (c)(1),
(2) Date: Jan. 8, 2018

(87) PCT Pub. No.: WO2016/131538
PCT Pub. Date: Aug. 25, 2016

(65) Prior Publication Data
US 2018/0169655 A1    Jun. 21, 2018

(30) Foreign Application Priority Data
Feb. 20, 2015   (DE) .................... 10 2015 001 998.8

(51) Int. Cl.
*B01L 3/00*       (2006.01)
*B01L 7/00*       (2006.01)
(Continued)

(52) U.S. Cl.
CPC ..... *B01L 3/502715* (2013.01); *B01L 3/50273* (2013.01); *B01L 7/52* (2013.01);
(Continued)

(58) Field of Classification Search
CPC .................. B01L 7/52; B01L 2300/0636; G01N 27/3276
See application file for complete search history.

(56) References Cited

U.S. PATENT DOCUMENTS 4,655,747 A * 4/1987 Allen, Jr. .............. A61M 5/284
                                                 604/191
6,448,064 B1 * 9/2002 Vo-Dinh .............. B01J 19/0046
                                                 435/183
(Continued)

FOREIGN PATENT DOCUMENTS

DE     102010043030 A1    5/2012
DE     102011056606 B3    1/2013
(Continued)

OTHER PUBLICATIONS

E. Ghafar-Zadeh et al., Novel direct-write CMOS-based laboratory-on-chip: Design, assembly and experimental results, 134 Sensors and Actuators A 2007, p. 27-36. (Year: 2007).*
(Continued)

*Primary Examiner* — C. Sun
(74) *Attorney, Agent, or Firm* — Frank Rosenberg

(57) ABSTRACT

A microfluidic cartridge having a detection chamber for detecting biomolecules in a sample solution. A CMOS-based microchip having a sensor area is arranged in the detection chamber and a contact area that is fluid-tightly separated from the detection chamber. The sensor area of the microchip including an array of functionalized test sites for electrochemically detecting biomolecules in the sample solution, and each test site in the sensor area is furnished with its own sigma-delta modulator for the analog-to-digital conversion of electrical signals produced at the test sites upon electrochemical detection.

15 Claims, 6 Drawing Sheets

Figure 1:
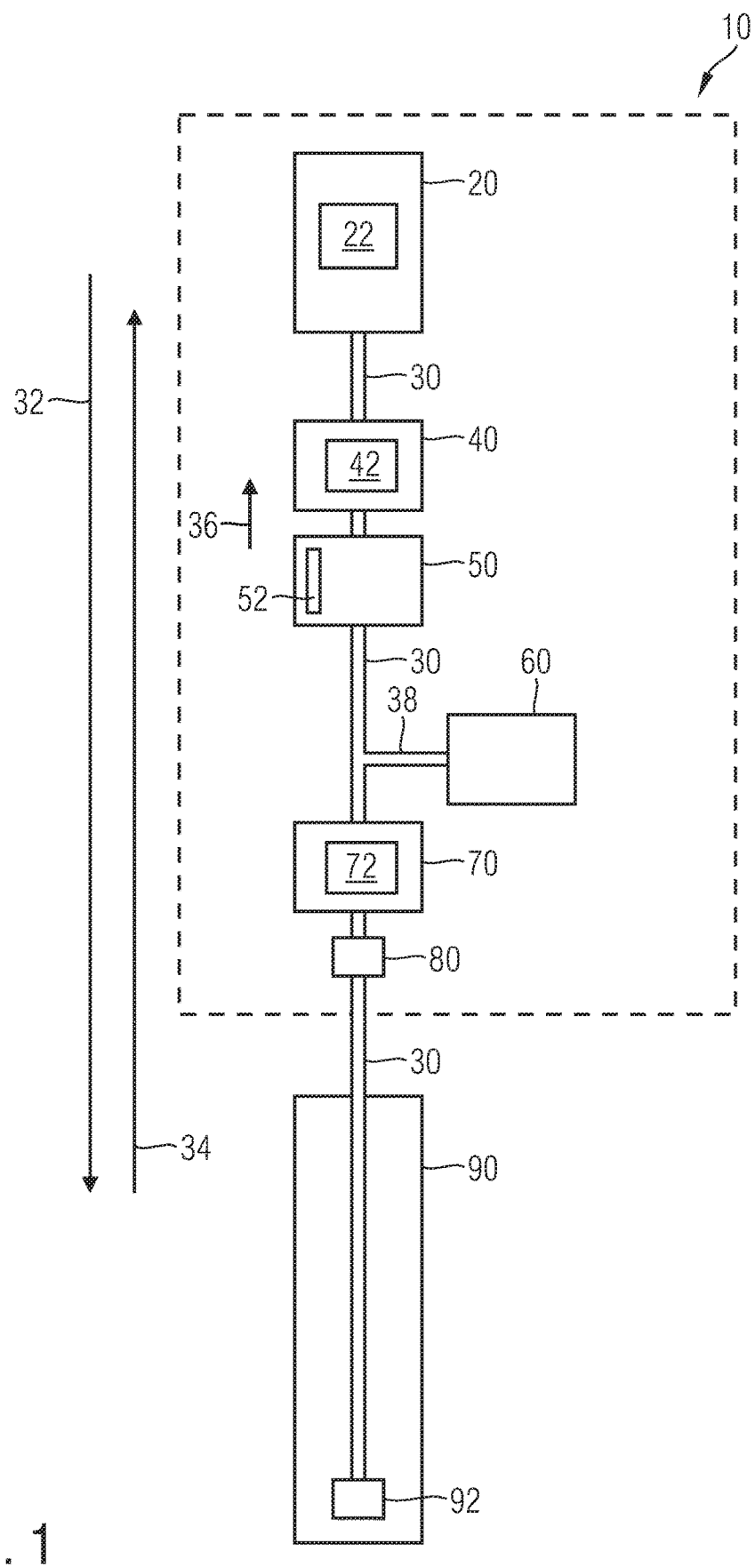

(51) Int. Cl.
*C12Q 1/6825* (2018.01)
*G01N 27/327* (2006.01)

(52) U.S. Cl.
CPC .. *G01N 27/3276* (2013.01); *B01L 2200/0684* (2013.01); *B01L 2200/16* (2013.01); *B01L 2300/0636* (2013.01); *B01L 2300/0645* (2013.01); *B01L 2300/0816* (2013.01); *B01L 2300/087* (2013.01); *B01L 2400/0478* (2013.01); *B01L 2400/0677* (2013.01); *C12Q 1/6825* (2013.01)

(56) References Cited

U.S. PATENT DOCUMENTS

| | | | | |
|---|---|---|---|---|
| 6,607,907 | B2* | 8/2003 | McNeely | B01J 19/0093 422/130 |
| 8,936,763 | B2* | 1/2015 | Rothberg | C12Q 1/6874 422/407 |
| 9,086,371 | B2 | 7/2015 | Clemens et al. | |
| 9,347,097 | B2* | 5/2016 | Gumbrecht | B01L 3/5027 |
| 2002/0045272 | A1* | 4/2002 | McDevitt | C12Q 1/37 436/518 |
| 2008/0149840 | A1 | 6/2008 | Handique | |
| 2008/0205017 | A1 | 8/2008 | Nelissen | |
| 2010/0276734 | A1* | 11/2010 | Josowicz | G01N 27/3277 257/253 |
| 2010/0280758 | A1* | 11/2010 | Hongo | C12Q 1/683 702/19 |
| 2011/0060530 | A1* | 3/2011 | Fennell | A61B 5/1473 702/19 |
| 2011/0201099 | A1* | 8/2011 | Anderson | G01F 23/292 435/287.2 |
| 2012/0088234 | A1 | 4/2012 | Hartwich et al. | |
| 2012/0100552 | A1 | 4/2012 | Welle et al. | |
| 2013/0137169 | A1* | 5/2013 | Kojima | G01N 21/6486 435/289.1 |
| 2014/0043049 | A1* | 2/2014 | Gupta | G01N 27/4148 324/693 |
| 2014/0073517 | A1* | 3/2014 | Zhou | C12Q 1/6813 506/9 |
| 2014/0318958 | A1 | 10/2014 | Hassibi et al. | |
| 2014/0329244 | A1 | 11/2014 | Ding | |

FOREIGN PATENT DOCUMENTS

| | | |
|---|---|---|
| EP | 1246699 B1 | 1/2007 |
| WO | 2004052527 A1 | 6/2004 |

OTHER PUBLICATIONS

B. Baker, How delta-sigma ADCs work, Part I, p. 13-18, 3Q 2011; Part II, p. 9, 4Q 2011; Texas Instruments Incorporated. (Year: 2011).*
Jafari, H.M., et al., "Nanostructured CMOS Wireless Ultra-Wideband Label-Free PCR-Free DNA Analysis SoC, IEEE Journal of Solid-State Circuits," vol. 49, No. 5, May 2014.
Machine translation of DE 102010043030 A1 of May 3, 2012.
Machine translation of DE 102011056606 B3 of Jan. 3, 2013.
Machine translation WO 2004052527 of Jun. 24, 2004.
International Preliminary Report on Patentability from International Application No. PCT/EP2016/000259, dated Feb. 10, 2017.
International Search Report from International Application No. PCT/EP2016/000259 mailed May 12, 2016.
Written Opinion from International Application No. PCT/EP2016/000259 mailed May 12, 2016.
Flavio Heer et al: "CMOS Electro-Chemical DNA-Detection Array with On-Chip ADC", ISSCC 2008 / Session 8 / Medical & Displays / 8.4; Jan. 2008.
Joerg Rothe et al: "Fully Integrated CMOS Microsystem for Electrochemical Measurements on 32 x 32 Working Electrodes at 90 Frames Per Second", Analytical Chemistry, 2014, 86 (13), 6425-6432.
Kruppa, P et al: "A digital CMOS-based 24x16 sensor array platform for fully automatic electrochemical DNA detection", Biosensors and Bioelectronics, 2010, 26 (4), 1414-1419.
Translation of International Preliminary Report on Patentability from International Application No. PCT/EP2016/000259, dated Feb. 10, 2017.
Translation of International Search Report from International Application No. PCT/EP2016/000259 mailed May 12, 2016.

* cited by examiner

MICROFLUIDIC CARTRIDGE FOR DETECTING BIOMOLECULES

RELATED APPLICATIONS

This application is the U.S. national stage application of International Application PCT/EP2016/000259, filed Feb. 16, 2016, which international application was published on Aug. 25, 2016 as International Publication WO 2016/131538. The International Application claims priority of German Patent Application No. 10 2015 001 998.8 filed on 20 Feb. 2015.

The present invention relates to a microfluidic cartridge for detecting biomolecules in a sample solution, and an associated detection method.

Numerous issues in molecular biology research and diagnostics require the determination of the amount or concentration of certain biomolecules, for example of certain nucleic acids in a sample. Within the scope of this description, the term nucleic acid here also comprises nucleic acid sequences.

Here, powerful and fast detection methods employ an array technology using so-called DNA chips, which enable a surface-sensitive detection of nucleic acid oligomer hybridization events. Often, an amplification step is included before the actual, already highly sensitive detection, in which the nucleic acids to be detected are replicated so that, ultimately, they are present in a concentration above the detection limit of the selected detection method.

Different methods for such a specific amplification of nucleic acids are known in the background art, for example polymerase chain reaction (PCR). PCR has become common in nearly all areas of science and medicine, including forensic medicine, prenatal diagnostics, oncology and, not least, in microbiological diagnostics. PCR is an enzymatic reaction for amplifying nucleic acids that takes place substantially in an aqueous or liquid reaction mixture with very small volumes. In the reaction mixture is a sample containing nucleic acid, as well as the primer, nucleotides and a polymerase that are also required for the reaction. By adding buffers and preferably divalent ions, the reaction mixture is adjusted in such a way that the optimum reaction conditions for the respective application type prevail.

PCR is based on a multiply repeating cycle of three steps, denaturation, hybridization and extension, that take place at different temperatures. In each cycle, the number of nucleic acids to be multiplied is roughly doubled such that a significant amplification can be achieved with a low number of cycles.

For further details and background information on PCR in general, on real-time PCR, in which the amount of nucleic acid is determined while the PCR reaction is in progress, and on preferred methods for electrochemically detecting nucleic acid oligomer hybridization events at test sites on a DNA chip, reference is made to applicant's document DE 10 2011 056 606 B3, whose disclosure is incorporated in the present application by reference.

A microfluidic device for processing bioparticles is known, for example, from document DE 10 2010 043 030 A1.

Proceeding from this, the object of the present invention is to create a microfluidic device that is economical to manufacture and enables easy and fast detection of biomolecules.

This object is solved by the features of the independent claims. Developments of the present invention are the subject of the dependent claims.

The present invention provides a microfluidic cartridge for detecting biomolecules in a sample solution, having a detection chamber to which the sample solution is suppliable through a feed channel, and from which the analyzed sample solution is drainable through an outlet channel, a CMOS-based microchip that comprises a sensor area arranged in the detection chamber and a contact area that is fluid-tightly separated from the detection chamber, the sensor area of the microchip including an array of functionalized test sites for electrochemically detecting biomolecules in the sample solution, and each test site in the sensor area being furnished with its own sigma-delta modulator for the analog-to-digital conversion of electrical signals produced at the test sites upon electrochemical detection.

The sigma-delta modulators are preferably first-order sigma-delta modulators that output, as a digitalized signal, a bit stream that is insensitive to noise and crosstalk. It is understood that, for complete analog-to-digital conversion, the bit stream output by the sigma-delta modulators is suitably further processed according to the principles of sigma-delta technology to provide the converted output signals at contact sites in the contact area.

In a development of the present invention, the microfluidic cartridge further comprises a reaction chamber, especially for the amplification of nucleic acids in the sample solution, from which the sample solution is suppliable to the detection chamber through the feed channel.

The sample solution in the reaction chamber is preferably heatable to a target temperature near its normal boiling point, and the reaction chamber, via a compensating channel, is in fluid communication with a pressure chamber that is liquid-free in normal operation, that is heatable to a temperature above the normal boiling point of the sample solution, and that is designed to evaporate a quantity of sample solution that is pushed through the compensating channel into the pressure chamber by gas bubbles in the sample solution and, in this way, to produce gas-bubble-reducing counterpressure on the sample solution present in the reaction chamber.

The microfluidic cartridge advantageously comprises, additionally, an integrated pump device that is in fluid communication with the reaction chamber and the detection chamber and that is configured to transfer the sample solution to the reaction chamber and from there in defined sample solution volumes to the detection chamber. The pump device is advantageously further configured to supply a process fluid provided in the pump device to an external sample system and, following enrichment of the process fluid in the external sample system with biomolecules to be detected, to return the sample solution thus created to the cartridge, especially to the reaction chamber, and from there in defined sample solution volumes to the detection chamber.

The microfluidic cartridge is expediently furnished with, for an external sample system, a connector that is especially developed as a Luer connector. A Luer connector is a standardized connecting system for tube systems in the medical field, in which the sealing of the connector is achieved by a conical design of the connecting parts, the so-called Luer cone. To secure the connection, the Luer cone can comprise a thread having a union nut and is then also referred to as a Luer lock. The connection closes and opens with a half turn. The term Luer connector also comprises the secured connection by a Luer lock.

In the microfluidic cartridge is advantageously developed a microchannel system that extends from the pump device via the detection chamber and the reaction chamber to the connector for the external sample system. Within the scope of this application, microchannels or microfluidic channels especially have a diameter or a largest transverse dimension of 0.5 mm to 3.2 mm.

To enable the execution of a PCR in a reaction chamber in the cartridge, in an advantageous development, the microfluidic cartridge, including the potentially integrated pump device, is formed from a PCR-suitable plastic, especially from polycarbonate. Here, the cartridge can be formed, for example, through an additive manufacturing method, such as 3D printing, through a forming process, such as hot stamping, or particularly preferably through an injection molding process.

In one preferred development, the pump device is developed as a double syringe for supplying a process fluid to a microchannel system in the cartridge. Here, the double syringe comprises:
- a cylindrical outer chamber that defines a reservoir for receiving process fluid,
- arranged within the outer chamber, a cylindrical inner chamber that comprises, in its distal cylinder base surface, an outlet opening for connecting with the microchannel system in the cartridge, and that is in fluid communication with the outer chamber via through holes,
- an inner piston that is axially movable in the inner chamber and that, in a closed position, closes the through holes on the inner chamber side, and in a release position, releases the through holes and enables a fluid flow from the outer chamber to the inner chamber, and
- an annular piston that in the outer chamber is axially movable toward the distal end of the outer chamber,
  i) that, in a proximal reservoir position, closes off the reservoir for the process fluid,
  ii) through whose movement toward the distal end a process fluid provided in the reservoir is pushed via the through holes into the inner chamber when the inner piston is in its release position, and
  iii) that, in a distal closed position, closes the through holes from the outer chamber side and, in this way, enables fluid to be drawn back from the microchannel system in the cartridge into the inner chamber by axially moving the inner piston toward the proximal end.

The present invention also includes a method for detecting biomolecules in a sample solution by means of a cartridge of the kind described, in which
- the sample solution is supplied to the detection chamber through a feed channel and drawn onto the sensor area, arranged in the detection chamber, of the CMOS-based microchip and
- a signal produced at the functionalized test sites upon electrochemical detection of the biomolecules is acquired and analyzed to detect the biomolecules in the sample solution.

Further advantageous steps of the method according to the present invention can be found in the description of the drawings below, especially the description of FIGS. 1 and 2.

Advantages of the present invention and further exemplary embodiments are explained below by reference to the drawings, in which a depiction to scale and proportion was dispensed with in order to improve their clarity.

Figure 2:
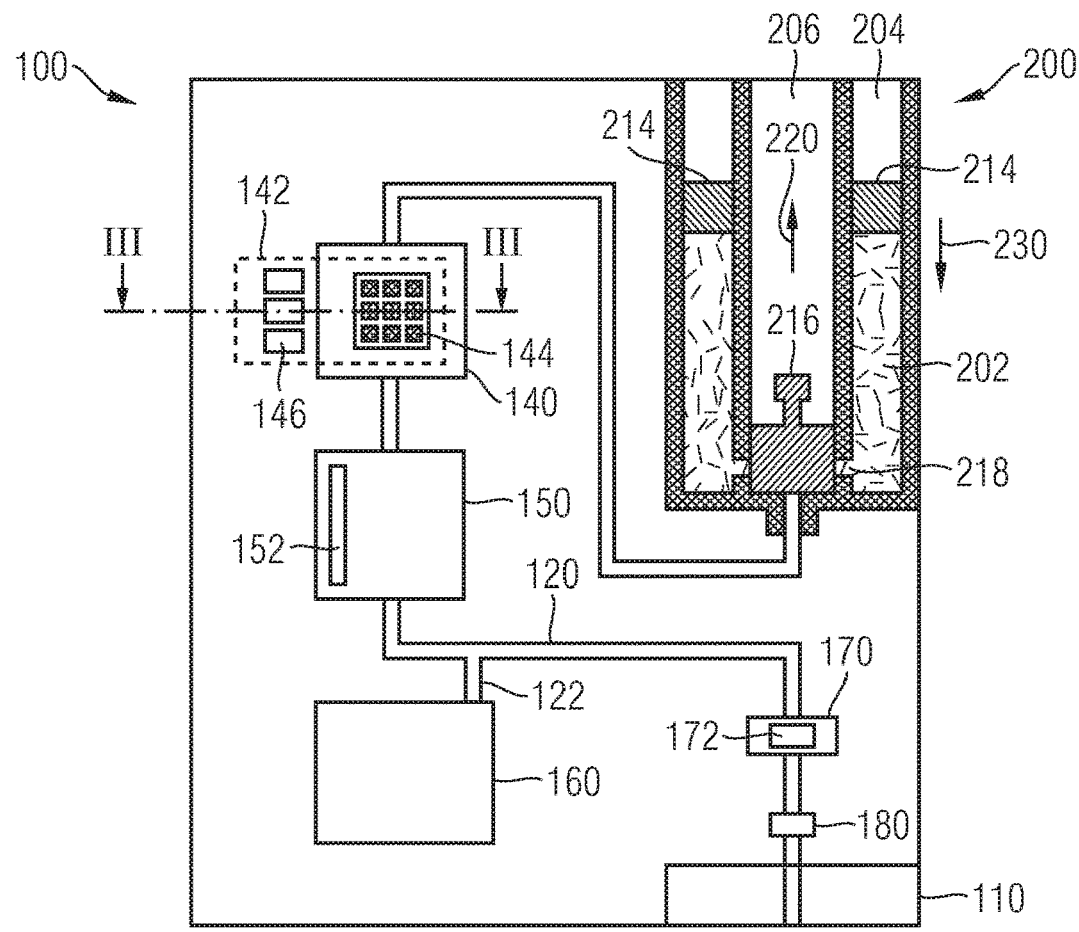
Figure 3:
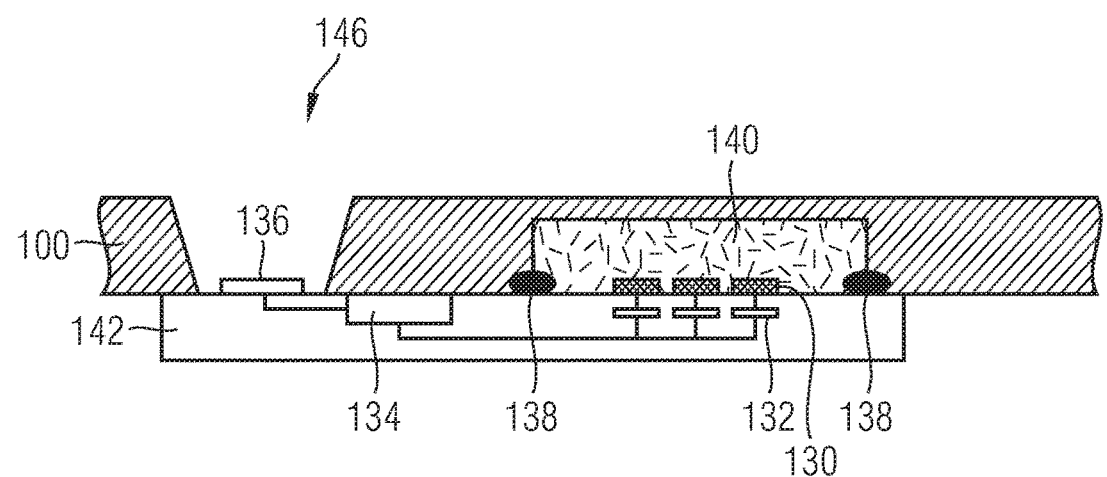
Figure 4:
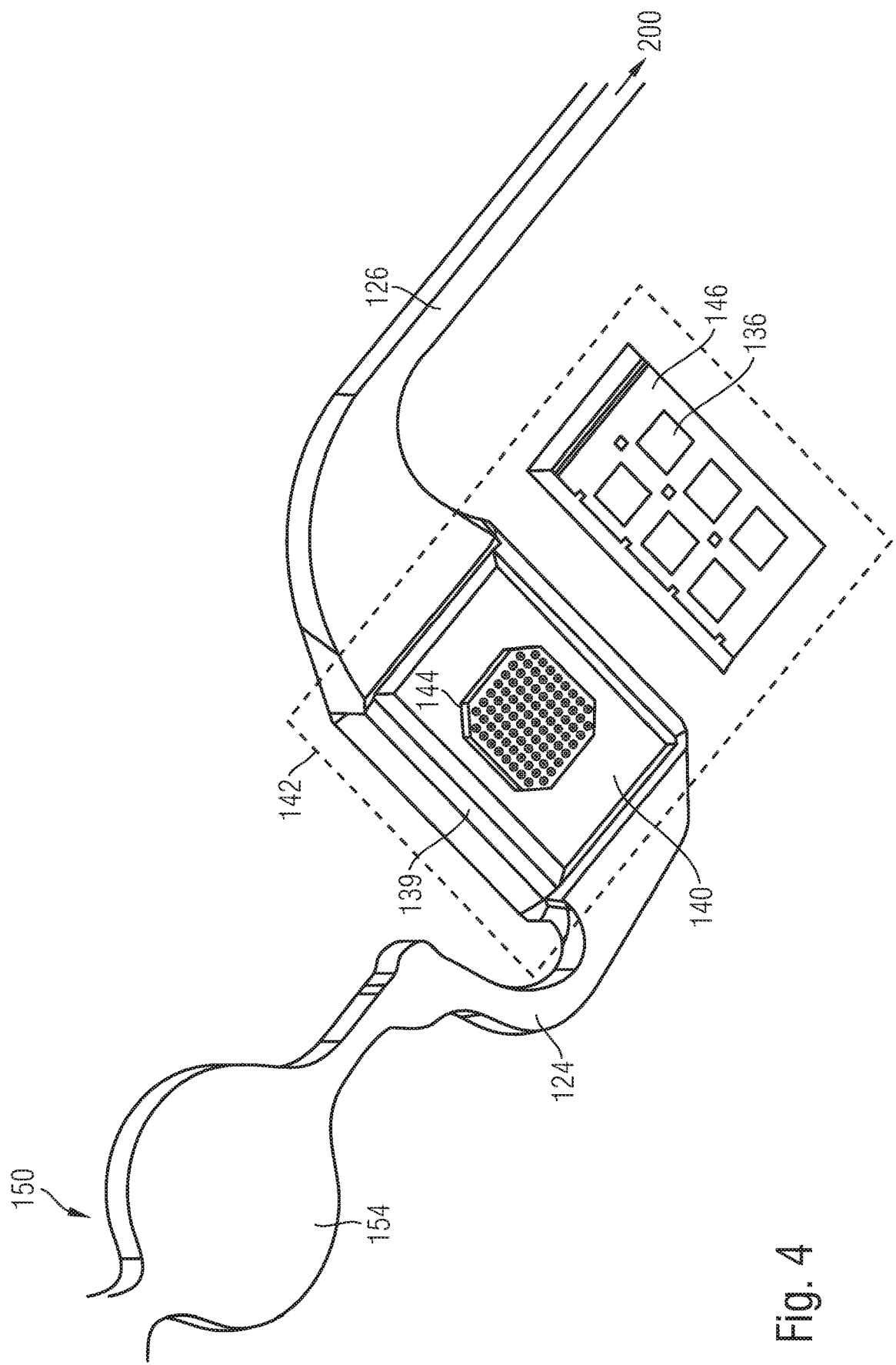
Figure 5:
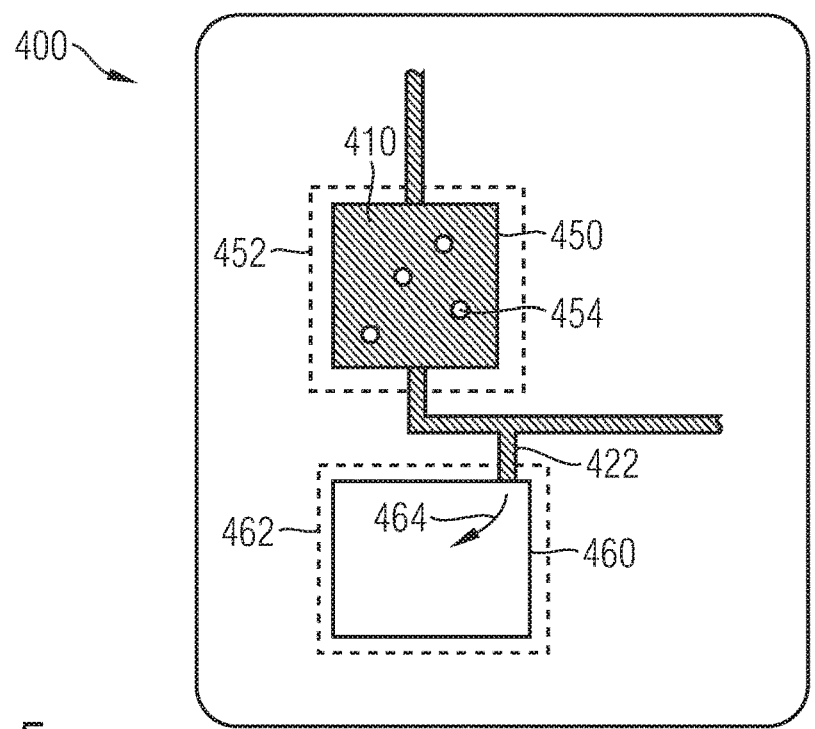
Figure 6:
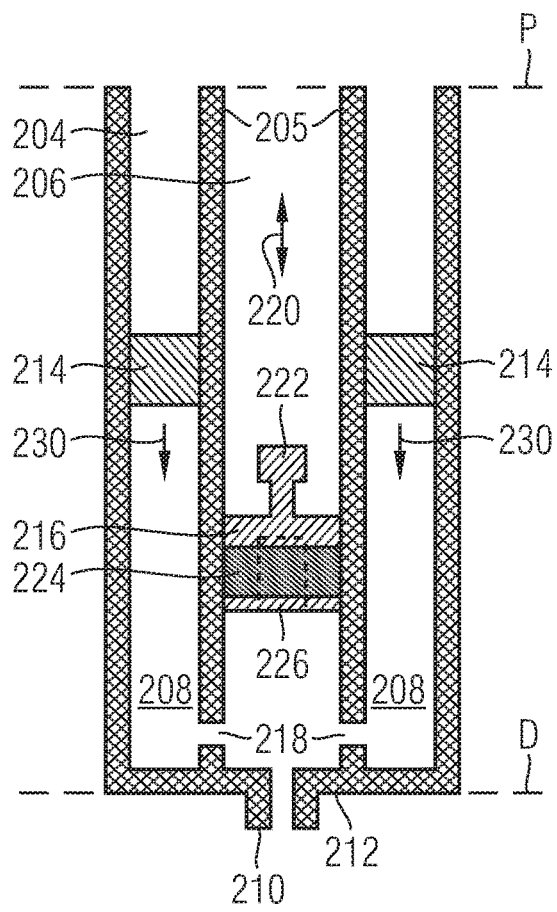
Figure 7:
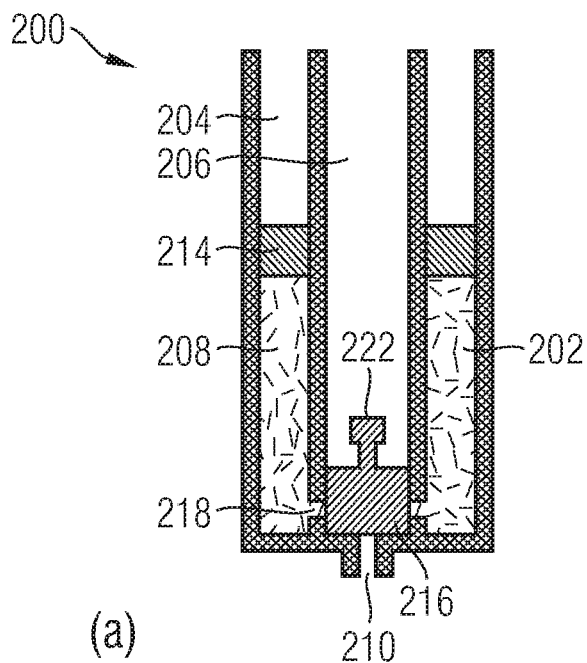
Figure 7:
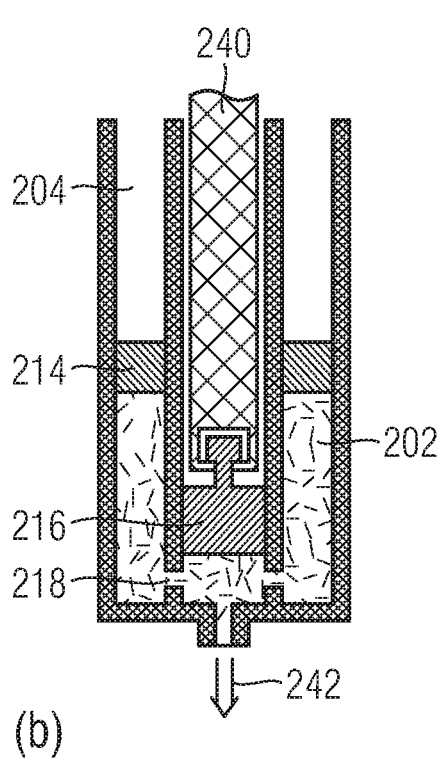
Figure 7:
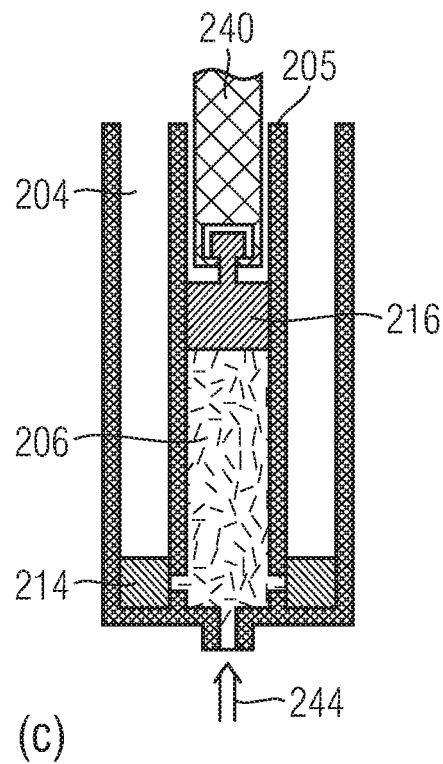
Figure 8:
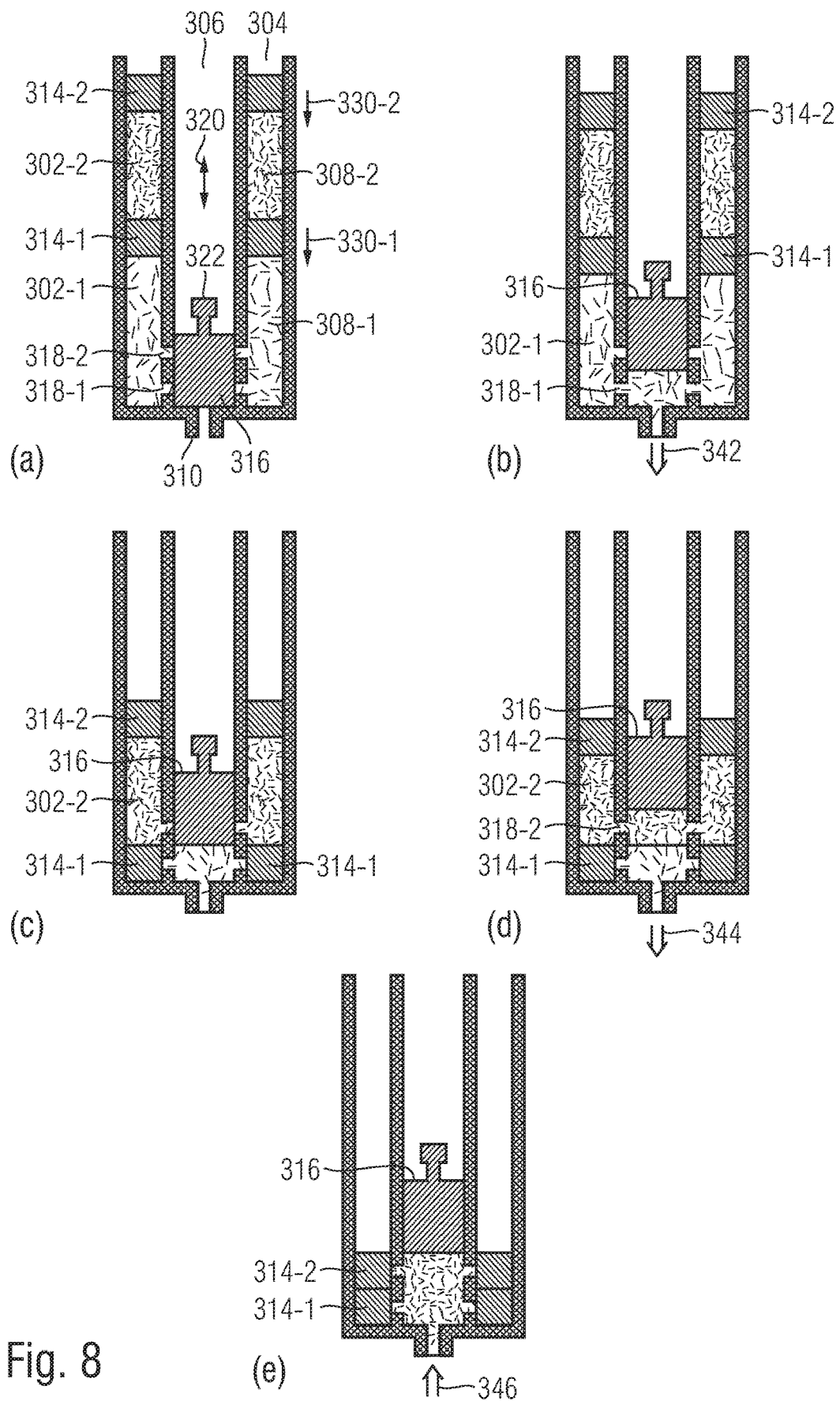

Shown are:

FIG. 1 a schematic depiction of the principle of the detection of nucleic acids in a sample by a detection system according to the present invention, FIG. 2 schematically, a microfluidic cartridge for detecting biomolecules in a sample solution according to an exemplary embodiment of the present invention, FIG. 3 schematically, a cross section of the cartridge in FIG. 2 in the area of the microchip along the line III-III, FIG. 4 a section of a microfluidic cartridge according to the present invention in the area of the detection chamber and the PCR chamber in perspective top view, FIG. 5 a section of a microfluidic device for temperature-controlledly processing biomolecules in a sample solution, FIG. 6 schematically in cross section, a double syringe that can be used as a pump device in a microfluidic cartridge, FIG. 7 in (a) to (c), the double syringe in FIG. 6 in different states when supplying/returning a fluid, and FIG. 8 in (a) to (e), a multifluid double syringe in different states when supplying/returning fluids.

FIG. 1 illustrates the principle of the detection of certain nucleic acids in a sample 92 present in a sample system 90 by a detection system 10. The sample 92 can be, for example, a patient's swab sample that is present on the end of a swab in a sample tube 90 and that is to be microbiologically examined for MRSA strains (methicillin-resistant *Staphylococcus aureus*).

The detection system 10 includes a pump device 20 having a process fluid 22 that, in a supply step, is supplied to the sample 92 through a microchannel system 30 and an open valve 80 (flow direction 32). On its way through the microchannel system 30, the process fluid 22 passes through a reservoir area 70 in which it receives chemicals 72 provided there, in the exemplary embodiment for instance to expose the DNA in the sample 92. The detection chamber 40, the reaction chamber 50 and the pressure chamber 60 in the detection system 10 do not yet play a role in this supply step.

Then, in a return step, the sample solution created in the sample system 90 by lysing the sample 92 is returned to the detection system 10 by the pump device 20 (flow direction 34). Here, the sample solution is normally drawn back all the way to the pump device 20 to ensure that at least the reaction chamber 50 in the detection system 10 is filled with sample solution. Following the return step, the valve 80 to the external sample system 90 is closed in order to have a defined fluid volume present in the detection system 10 and to obtain a closed system.

To amplify the nucleic acids to be detected, a polymerase chain reaction (PCR) is carried out in the reaction chamber 50. The chemicals 52 required for this are initially present preassembled and protected under a wax layer. At the start of the amplification, the wax layer is melted by a temperature increase, and in this way, the PCR chemicals 52 are added to the sample solution in the reaction chamber 50. During the PCR, the melted wax remains fluid or is taken up by multiple reservoirs in the edge region of the reaction chamber 50 to ensure that no solidified wax clogs adjoining microchannels 30.

The cyclical temperature profile in the reaction chamber 50 required for the PCR is produced with the aid of a heating/cooling device (not shown) assigned to the reaction chamber 50. The controlled progress of the PCR, which is not a matter of course in microfluidic systems, is ensured in the detection system 10 by a pressure chamber 60 that is in fluid communication with the reaction chamber 50 via a compensating channel 38. As explained in greater detail below, the pressure chamber 60 is liquid-free in normal operation and is kept at a temperature significantly above the normal boiling point of the sample solution, for example $T_{DK}=120°$ C., by a heating device (not shown) assigned to the pressure chamber.

Any gas bubbles arising in the reaction chamber 50 in the denaturing step at T≈96° C. press a small amount of the sample fluid into the pressure chamber 60, where it immediately evaporates due to the increased pressure chamber temperature. Due to the large gas volume produced upon evaporation, there is rapidly created in the pressure chamber 60 on the sample solution present in the reaction chamber 50 a counterpressure that strongly reduces the number and size of the gas bubbles. In this way, the reaction chamber 50 and the pressure chamber 60 form a self-regulating subsystem for suppressing undesired gas bubbles in the reaction chamber 50 and, in this way, ensure well-controlled progress of the PCR.

Specifically, in the detection system 10, a particular type of PCR is carried out that is referred to as real-time PCR, since here, the amount of nucleic acid present in the sample solution is determined while the reaction is taking place. Real-time PCR permits a more precise determination of the concentration of the nucleic acid in the sample solution than a pure end-point determination at the end of a PCR. In the real-time PCR carried out in the detection system 10, first, a first predetermined number of cycles of the amplification reaction are carried out, for example 15 cycles, to raise the concentration of nucleic acid in the measuring range.

Subsequently, with the aid of the pump device 20, a defined volume of sample solution having amplified nucleic acids is transferred from the reaction chamber 50 to the detection chamber 40 (flow 36). In the detection chamber is arranged the sensor area 42 of a CMOS-based microchip, which sensor area comprises an array of functionalized test sites for electrochemically detecting the nucleic acids in the sample solution. Upon electrochemical detection, the test sites each produce an electrical signal whose size constitutes a measure for the concentration of nucleic acid in the transferred detection volume. One preferred electrochemical detection method is described in document DE 10 2011 056 606 B3, whose disclosure is incorporated in the present application by reference.

Subsequently, one further PCR cycle is repeatedly carried out each time to further increase the concentration of nucleic acid, and after each cycle, a defined volume of sample solution having amplified nucleic acids is transferred from the reaction chamber 50 to the detection chamber 40, and the concentration of nucleic acid electrochemically determined. In this way, a total of 30 to 40 PCR cycles, for example, can be carried out. At the end of the process, to determine the endpoint, another, larger final volume of sample solution can be drawn into the detection chamber 40 and the concentration of nucleic acid electrochemically detected.

As a specific implementation of a detection system 10, FIG. 2 shows, schematically, an exemplary embodiment in the form of a microfluidic cartridge 100 for detecting biomolecules in a sample solution that is constructed according to the principles explained in connection with FIG. 1.

The cartridge 100 is, with the exception of the provided chemicals and the microchip 142, completely formed from polycarbonate, for example by an additive manufacturing method or by injection molding. The cartridge 100 is a single-use cartridge for an economical detection of desired nucleic acids, for example in a MRSA screening.

For the connection with a sample system, the cartridge 100 comprises a Luer connector 110 to which, for example, a sample tube 90 having a swab specimen 92 to be analyzed can be connected.

Developed in the cartridge 100 is a microchannel system 120 that extends from a pump device 200 via a detection chamber 140, a PCR chamber 150 having PCR chemicals 152 protected by a wax layer, and a reservoir 170 for lysing chemicals 172 to the Luer connector 110. In other embodiments, the lysing chemicals 172 are provided at another location, for example in the Luer connector or in the sample tube 90.

The pump device is designed in the form of the double syringe 200 explained in greater detail below and forms an integral part of the polycarbonate cartridge 100. Here, an outer chamber 204 of the double syringe 200 is storage-stably prefilled with a desired process fluid 202 such that the cartridge 100 includes, with the exception of the heating/cooling device, substantially all the components needed for the desired detection.

To determine the concentration of the nucleic acids in the sample solution, the cartridge includes a CMOS-based microchip 142 whose contour is marked as a dotted line in FIG. 2. The microchip 142 comprises a sensor area 144 arranged in the detection chamber 140 and a contact area 146 that is fluid-tightly separated from the detection chamber. For a more precise explanation, FIG. 3 shows, schematically, a cross section of the cartridge 100 in the area of the microchip 142 along the line III-III in FIG. 2.

The sensor area 144 of the microchip 142 includes an array of, for example, 109 functionalized test sites 130 in an octagonal arrangement for electrochemically detecting the nucleic acids to be detected in the sample solution. Here, a suitable detection method is described, for example, in document DE 10 2011 056 606 B3.

For a particularly good readout result, each of the test sites 130 in the sensor area 144 is furnished with its own first-order sigma-delta modulator 132 for the AD conversion of the electrical signals produced at the test sites 130. The sigma-delta modulators 132 output, as a digitalized signal, a bit stream that is insensitive to noise and crosstalk, but that is further processed for the complete AD conversion according to the per se known principles of sigma-delta technology in a processing circuit 134 to produce the final output signals. The output signals can be tapped at the contact pads 136 in the contact area 146 of the microchip 142 and supplied to an analysis and display unit in the usual manner.

As shown in FIG. 3, the contact area 146 of the microchip 142 is fluid-tightly separated, for example by means of a rubber ring 138 or a casting compound, from the detection chamber 140 with the sample solution contained therein in operation.

To analyze a sample 92, the cartridge 100 is first connected with the sample system 90 via the Luer connector 110, and the valve 180, if not already open, is opened. Now, by slightly raising 220 the inner piston 216 of the double syringe 200 with an associated piston rod (FIG. 7(b)), the through holes 218 between the outer chamber and the inner chamber 206 can be released. By pressing down 230 the rubber ring 214, the provided process fluid 202 is supplied to the sample 92 via the microchannel system 120, whereby the process fluid in the reservoir 170 receives the lysing chemicals 172.

The pressed-down rubber ring 214 closes the through holes 218 from the outer chamber side such that, through a further axial movement of the inner piston 216 with the piston rod, the sample solution generated by lysing the sample 92 can be drawn back into the microchannel system 120 of the cartridge 100 into the inner chamber 206 of the double syringe 200. In this state, the channel system 120 including the PCR chamber 150 and the detection chamber 140 is filled with sample solution. The pressure chamber 160 that is in fluid communication with the PCR chamber 150 via the compensating channel 122, in contrast, remains substantially liquid-free. Then the valve 180 to the external sample system 90 is closed in order to have a defined enclosed fluid volume in the detection system for the subsequent PCR.

For carrying out the PCR, the cartridge 100 can be used, for example, in a thermocycler, which provides heating/cooling devices for the temperature steps of the PCR cycles. In particular, in the PCR chamber 150, the PCR chemicals 152 are added to the sample solution by melting the wax layer and the PCR is carried out by producing the desired cyclical temperature profile. In addition, as described in greater detail below, by heating up the pressure chamber 160 to a temperature $T_{DK}$ above the boiling temperature of the sample solution, formation of gas bubbles in the PCR chamber 150 is suppressed such that the PCR can proceed in a reliable and controlled manner.

Following a predetermined number of initial PCR cycles, a defined volume of sample solution having amplified nucleic acids is transferred from the PCR chamber 150 to the detection chamber 140 by controlledly raising the inner piston 216 of the double syringe. The desired concentration values of nucleic acid in the sample solution are determined by electrochemically detecting the nucleic acid oligomer hybridization events at the test sites 130 on the microchip 142, as described in greater detail in DE 10 2011 056 606 B3.

After each further PCR cycle, a further defined volume of further amplified sample solution is transferred in each case from the PCR chamber 150 to the detection chamber 140 by successively raising the inner piston 216, and the concentration of nucleic acid is determined. For example, the PCR chamber 150 can have a volume of 30 µl and, after completion of the initial PCR cycles, for 15 to 25 cycles, a volume of 1 µl is transferred to the detection chamber 140 after each PCR cycle. At the end of the process, a larger final volume of sample solution can, in addition, be drawn into the detection chamber 140 and a concentration endpoint determined. It is understood that the concentration determination can also be carried out at greater intervals, for example after each second or each third PCR cycle.

A concrete design of the cartridge 100 in the area of the detection chamber 140 and the PCR chamber 150 is shown in FIG. 4 in perspective top view for an exemplary embodiment. In said exemplary embodiment, the PCR chamber 150 is divided into multiple successively arranged, disk-shaped sub-chambers 154, of which, in the drawing, only the last sub-chamber 154 is depicted. From the PCR chamber 150 or the last sub-chamber 154, a feed channel 124 leads to the detection chamber 140, from which an outlet channel 126 extends to the double syringe 200.

The contour of the CMOS-based microchip 142 is again marked with a dotted line. Here, the sensor area 144 of the microchip 142 having the array of test sites 130 is arranged in the detection chamber 140 and is fluid-tightly separated from the contact area 146 having the contact pads 136 by a circumferential casting compound ring 139.

The self-regulating sub-system for suppressing gas bubbles in the PCR chamber is explained again in greater detail in FIG. 5. The described principle is not limited to application in a PCR, but rather can also be used in other temperature-controlled microfluidic processing operations in which a sample solution is to be maintained free of gas bubbles near the normal boiling point of the sample solution.

FIG. 5 shows a section of a microfluidic device 400 for temperature-controlledly processing a sample solution 410, here the above-described detection of nucleic acids. The microfluidic device 400 includes a reaction chamber 450 in which the sample solution having the nucleic acids is heatable by a heating/cooling device 452 to a target temperature near the normal boiling point of the sample solution 410. In the above-mentioned real-time PCR, the sample solution 410 is, for example, heated to about 96° C. in the denaturing step.

In microfluidic devices, gas bubbles can not only lead to large temperature differences in the sample solution in the reaction chamber 450, but also to sample solution being pressed out of the reaction chamber and to strong fluid oscillation in the microfluidic system. Several measures have been suggested to suppress the creation of gas bubbles in microfluidic PCR systems, such as a special structural design of the reaction chamber, a surface treatment of the reaction chamber walls, a sealing of the reaction chamber under increased pressure, a degassing of the sample solution and the addition of reagents with a high boiling point.

In the advantageous solution used here, gas bubbles are suppressed in the reaction chamber 450 by a fluidic coupling of the reaction chamber 450 to a pressure chamber 460 that is liquid-free in normal operation and has a temperature above the normal boiling point of the sample solution 410. As depicted in FIG. 5, the reaction chamber 450 is, via a compensating channel 422, in fluid communication with a pressure chamber 460 that, by means of a heating device 462, is heated to a temperature $T_{DK}$ significantly above the normal boiling point of the sample solution. In the exemplary embodiment, the pressure chamber temperature is between 110° C. and 130° C., for example $T_{DK}$=125° C. Since the pressure chamber temperature is above the boiling temperature, the pressure chamber 460 is liquid-free in normal operation.

Without wanting to be bound to a specific explanation, the mechanism of gas bubble suppression is currently understood as follows: In the event that, in the temperature-controlled processing of the biomolecules, such as the above-mentioned PCR denaturing step, gas bubbles 454 are created in the reaction chamber 450, then a small quantity of sample solution 464 is pressed by the first forming gas bubbles via the compensating channel 422 into the pressure chamber 460, where it immediately evaporates due to the high temperature prevailing in the pressure chamber 460. The gas volume created by the evaporation is 1,000 to 2,000 times larger than the volume of the evaporated fluid, such that a strong pressure increase results in the pressure chamber 460, which in turn leads to a pressure increase in the reaction chamber 450 and thus to a reduction in the number and size of the gas bubbles and counteracts the formation of further gas bubbles. The main effects here, according to current understanding, are the increase in the vapor pressure and the compression of the existing gas volumes.

Since the intensity of the counterpressure produced increases with the amount of fluid evaporated, and thus with the fluid volume 464 displaced by the gas bubbles, this approach leads to a self-regulation of the gas bubbles 454 in the sample solution 410. The pressure chamber 460 can easily be integrated into a microfluidic system and requires, for the suppression of the gas bubble formation, no complex designs of the reaction chamber, additions to the sample solution or other complex measures that normally either can prevent only a nucleation of gas bubbles on the reactor walls anyway or, as in the case of additions to the sample solution, can affect the progress of the PCR.

For supplying process fluid 202 to a microfluidic system, such as the microchannel system 120, 140, 150, 170, 180 in FIG. 2, advantageously, a double syringe 200 is used whose construction and functional principle will now be explained in greater detail with reference to FIG. 6.

The double syringe 200 includes two concentrically arranged cylinder chambers 204, 206, in each of which are included axially movable pistons 214, 216. In the present description, the end of the double syringe 200 comprising the outlet opening 210 is referred to as the distal end D of the syringe or cylinder, the axially opposite end as the proximal end P. More precisely, the double syringe includes a cylindrical outer chamber 204 that defines a reservoir 208 for the process fluid 202. Concentrically arranged in the outer chamber 204 is a cylindrical inner chamber 206 that closes at its distal end with the outer chamber 204. The outlet opening 210 of the double syringe is arranged in the distal cylinder base surface 212 of the inner chamber 206. The two cylinder chambers 204, 206 are in fluid communication with each other via an array of through holes 218 that are developed in the distal end area of the chambers 204, 206 circumferentially at the same axial level in the shared cylinder wall 205 of the inner and outer chamber.

Included in the inner chamber 206 is an axially movable inner piston 216 that comprises, on its proximal side, a grip element 222 that can be gripped from outside with a separate, adapted piston rod 240 (FIG. 7(b)) to be able to move the inner piston 216 axially up and down (arrows 220). In place of the grip element 222, there can, for example, also be developed in the proximal side of the inner piston 216 a cavity into which the appropriately developed distal end of a piston rod engages.

If the inner piston 216 is located at the distal end of the inner chamber 206, then the inner piston 216 closes the through holes 218 from the side of the inner chamber with a circumferential seal 224, for example a rubber seal, such that no fluid flow is possible from the reservoir 208 in the outer chamber 204 to the outlet opening 210. Said position of the inner piston 216 is thus referred to as the closed position and is shown in FIG. 7(a).

If the inner piston 216 is moved somewhat toward proximal, that is, in the orientation in FIG. 6, raised, then it releases the through holes 218 and enables a fluid flow from the outer chamber 204 via the inner chamber 206 to the outlet opening 210. Such a position of the inner piston 216 is therefore referred to as the release position and is shown in FIG. 7(b).

In the outer chamber 204 is included an annular sealing outer piston that surrounds the inner chamber 206, here in the form of a rubber ring 214, that is axially movable toward the distal end D of the outer chamber (arrows 230). In a proximal reservoir position, the rubber ring 214 closes off the reservoir 208 for the process fluid 202, as depicted in FIG. 7(a). In a distal closed position that is shown in FIG. 7(c), the rubber ring 214 closes the through holes 218 from the side of the outer chamber 204 and, in this way, enables fluid to be drawn back from the microfluidic system into the inner chamber 206 by axially moving the inner piston 216 toward the proximal end P of the syringe.

On the proximal side of the inner piston 216, a reservoir 226 can be provided for receiving chemicals. Here, the chemicals are initially fixed in the reservoir 226, but can be released at a desired time by a release function, for example a meltable wax cover or a magnetic particle cover layer.

The operating principle of the double syringe 100 will now be explained in greater detail with reference to FIGS. 7(a) to 7(c), in which a process fluid 202 provided in the outer chamber 204 of the double syringe 200 is supplied to a microfluidic system, which itself is not shown.

In the initial state in FIG. 7(a), the inner piston 216 is located in its distal closed position, and the rubber ring 214, in its proximal reservoir position. The reservoir 208 of the outer chamber 206 is storage-stably prefilled with the desired process fluid 202.

If the process fluid 202 is to be supplied to the microfluidic system, then the grip element 222 of the inner piston 216 is gripped with an adapted piston rod 240 and raised into the release position shown in FIG. 7(b), in which the through holes 218 release the fluid flow from the reservoir 208 of the outer chamber 204 to the outlet opening 210. The process fluid 202 can be completely pumped into the microfluidic system (flow 242) by pressing down the rubber ring 214.

As depicted in FIG. 7(c), the rubber ring 214 and the position of the through holes 218 in the cylinder wall 205 are coordinated with each other in such a way that, in its distal closed position, the rubber ring 214 closes the through holes 218 from the outer chamber side.

In this state, the double syringe can be used like an ordinary syringe by moving the piston rod 240 axially upward and downward in the inner chamber 206, and fluid can be moved in both directions. In particular, by further raising the inner piston 216, that is, moving it axially toward the proximal end, fluid can be drawn from the microfluidic system into the inner chamber 206 (flow 244).

In this way, in the exemplary embodiment in FIG. 2, for example, the sample solution created by lysing the sample 92 is drawn back from the sample tube 90 into the microchannel system in the cartridge 100, and finally into the inner chamber 206 of the double syringe. Also while carrying out the PCR, after each PCR cycle, small fluid volumes are successively transferred from the PCR chamber 150 to the detection chamber 140 by controlledly raising the piston rod 240.

With such a double syringe, given a suitable design, also two or more fluids can be supplied to a microfluidic system. FIG. 8 shows such a multifluid double syringe that, by way of example, is designed for supplying n=2 fluids to a microfluidic system. The expansion to supplying three and more fluids results freely from the following description.

Also the 2-fluid double syringe 300 in FIG. 8 includes two concentrically arranged cylinder chambers 304, 306 and thus constitutes a double syringe. The cylindrical outer chamber 304 defines n=2 reservoirs 308-1, 308-2 for receiving the fluids 302-1, 302-2 to be supplied.

Concentrically arranged in the outer chamber 304 is a cylindrical inner chamber 306 that closes at its distal end with the outer chamber 304. The outlet opening 310 of the double syringe 300 is arranged in the distal cylinder base surface of the inner chamber 306.

The two cylinder chambers 304, 306 are in fluid communication with each other via n=2 groups of through holes 318-1, 318-2 spaced apart in the axial direction. Here, each group of through holes 318-1, 318-2 consists of an array of through holes developed circumferentially at the same axial level in the shared cylinder wall 305 of the inner and outer chamber.

Included in the inner chamber 306 is an axially movable inner piston 316 that comprises, on its proximal side, a grip element 322 that can be gripped from outside with a separate, adapted piston rod to be able to move the inner piston 316 axial up and down (arrows 320). Here, too, in place of the grip element 322, a cavity, for example, can be developed in the proximal side of the inner piston 316 into which the distal end of an appropriately developed piston rod engages.

If the inner piston 316 is located at the distal end of the inner chamber 306 as in the initial position shown in FIG. 8(a), then the inner piston 316 having a circumferential rubber seal closes the n=2 groups of through holes 318-1, 318-2 from the side of the inner chamber such that no fluid flow is possible from the reservoirs of the outer chamber 304 toward the outlet opening 310. Said position of the inner piston 316 is therefore referred to as the closed position.

If the inner piston 316 is moved slightly proximally, it initially releases only the first group of through holes 318-1 and enables a fluid flow of the first fluid 302-1 from the outer chamber 304 via the inner chamber 306 to the outlet opening 310. Said position of the inner piston 316 is referred to as the first release position and is illustrated in FIG. 8(b). Through a further proximal movement, the inner piston 316 reaches the second release position, in which also the second group of through holes 318-2 is released from the inner chamber side (see FIG. 8(d)).

In the general case, there are n axially spaced release positions in which the inner piston 316 successively releases an increasing number k=1, . . . , n of groups of through holes and enables a corresponding fluid flow from the outer chamber to the inner chamber.

Included in the outer chamber 304, surrounding the inner chamber 306, are n=2 axially spaced rubber rings 314-1, 314-2 that are each movable axially toward the distal end D of the outer chamber (arrows 330-1, 330-2). In a proximal reservoir position, the rubber rings 314-1, 314-2 each close off a reservoir for one of the suppliable fluids 302-1, 302-2, as shown in FIG. 8(a).

In a distal closed position, the first rubber ring 314-1 closes the first group of through holes 318-1 (see FIG. 8(c)), while the second rubber ring 314-2, in its distal closed position, closes the second group of through holes 318-2 (see FIG. 8(e)).

If the inner piston 316 is located in its first or second release position, the fluid provided in the first or second reservoir can be successively pressed into the inner chamber 306 via the first or second group of through holes 318-1, 318-2 by moving the two rubber rings 314-1, 314-2 or only the second rubber ring 314-2 toward the distal end. If both rubber rings 314-1, 314-2 are brought into their distal closed position, then all through holes are closed and the fluid can be drawn back from the microfluidic system into the inner chamber 306 by moving the inner piston 316 proximally.

Proceeding from the initial state in FIG. 8(a), the grip element 322 of the inner piston 316 is gripped with an adapted piston rod and raised into the first release position (FIG. 8(b)). The first process fluid 302-1 can be completely pumped into the microfluidic system (flow direction 342) by pressing down the two rubber rings 314-1, 314-2. Here, due to the incompressibility of the fluids, it is sufficient to actively press the uppermost of the n rubber rings, here the rubber ring 314-2, toward distal. The applied pressure is transmitted to the first rubber ring 314-1 via the incompressible second process fluid 302-2 such that the two rubber rings move toward distal at a constant distance and the volume of the reservoir 308-2 remains unchanged upon supplying the first process fluid 302-1 (cf. FIGS. 8(a) and 8(c)).

The first rubber ring 314-1 and the position of the first group of through holes 318-1 in the cylinder wall 305 are coordinated with each other in such a way that, in its distal closed position, the first rubber ring 314-1 closes the first group of through holes 318-1 from the outer chamber side, as shown in FIG. 8(c).

Now the inner piston 316 can be further raised into the second release position (FIG. 8(d)), and the second process fluid 302-2 be completely pumped into the microfluidic system (flow direction 344) by pressing down the second rubber ring 314-2. Here, the second rubber ring 314-2 and the position of the second group of through holes 318-2 in the cylinder wall 305 are coordinated with each other in such a way that, in its distal closed position, the second rubber ring 314-2 closes the second group of through holes 318-1 from the outer chamber side, as shown in FIG. 8(e).

Since all rubber rings 314-1, 314-2 are now in their distal closed position, by moving the inner piston 316 and the piston rod axially up and down, the double syringe 300 can be used like an ordinary syringe and fluid can be moved in both directions. In particular, by further raising the inner piston 316, that is, moving it axially toward the proximal end, fluid can be drawn from the microfluidic system into the inner chamber 306 (flow direction 246).

In a multifluid double syringe having n annular pistons, the first n−1 distal annular pistons need not necessarily be sealing. For example, to reduce friction, the annular piston 314-1 of the double syringe 300 can be developed having some allowance to the cylinder walls of the inner or outer chamber, while the proximal annular piston 314-2 is developed to be sealing in order to storage-stably close off the reservoirs for the fluids 302-1, 302-2 to be supplied. In practice, there is no diffusion or mixing of the fluids through a narrow allowance gap of the annular piston 314-1, or it is, in any case, negligibly low.

In a simpler embodiment, there also need not be n axially spaced groups of through holes and n axially spaced release positions. Rather, it is already sufficient if the inner chamber is in fluid communication with the outer chamber via one or more groups of through holes spaced in the axial direction, and the inner piston, in a closed position, closes the one or more groups of through holes on the inner chamber side and, in one or more release positions, enables a fluid flow from the outer chamber to the inner chamber. Also in such a simpler embodiment, by moving the annular piston in the outer chamber toward the distal end, a fluid provided in the k-th reservoir can be pressed successively into the inner chamber via through holes if the inner piston is in a corresponding release position. If fewer than n groups of through holes are present, not every one of the n annular pistons must close a group of through holes, it must merely be ensured that the n annular pistons, in their distal closed position, together close the one or more groups of through holes from the outer chamber side such that a drawing back of fluid from the microfluidic system into the inner chamber by axially moving the inner piston toward the proximal end is enabled when all n annular pistons are brought into their distal closed position.

The invention claimed is:

1. A microfluidic cartridge for detecting biomolecules in a sample solution, comprising
   a detection chamber to which the sample solution is suppliable through a feed channel, and from which the analyzed sample solution is drainable through an outlet channel,
   a CMOS-based microchip that comprises a sensor area arranged in the detection chamber and a contact area that is fluid-tightly separated from the detection chamber, the sensor area of the microchip including an array of functionalized test sites for electrochemically detecting biomolecules in the sample solution, and each test site in the sensor area being furnished with its own sigma-delta modulator for the analog-to-digital conversion of electrical signals produced at the test sites upon electrochemical detection; each sigma-delta modulator being integrated in the microchip and adapted to output, as a digitalized signal, a bit stream; and the microchip including a processing circuit for receiving the bit stream output by each sigma-delta modulator and processing the bit stream output according to the principles of sigma-delta technology to provide the processed output signals to contact pads in the contact area.

2. The microfluidic cartridge according to claim 1, characterized in that the contact area is fluid-tightly separated from the detection chamber by means of a rubber ring or a circumferential casting compound ring.

3. The microfluidic cartridge according to claim 1, characterized in that the cartridge comprises a reaction chamber for the amplification of nucleic acids in the sample solution, from which the sample solution is suppliable to the detection chamber through the feed channel.

4. The microfluidic cartridge according to claim 3, characterized in that the sample solution in the reaction chamber is heatable to a target temperature near its boiling point and the reaction chamber, through a compensating channel, is in fluid communication with a pressure chamber that is liquid-free in operation, that is heatable to a temperature above the boiling point of the sample solution, and that is designed to evaporate a quantity of sample solution that is pushed via the compensating channel into the pressure chamber by gas bubbles in the sample solution and, in this way, to produce gas-bubble-reducing counterpressure on the sample solution present in the reaction chamber.

5. The microfluidic cartridge according to claim 1, characterized in that the cartridge comprises an integrated pump device that is in fluid communication with a reaction chamber and the detection chamber and that is configured to transfer the sample solution to the reaction chamber and from there in defined sample solution volumes to the detection chamber.

6. The microfluidic cartridge according to claim 5, characterized in that the pump device is further configured to supply a process fluid provided in the pump device to an external sample system and, following enrichment of the process fluid in the external sample system with biomolecules to be detected, to supply the sample solution thus created to the reaction chamber, and from there in defined sample solution volumes to the detection chamber.

7. The microfluidic cartridge according to claim 1, characterized in that the cartridge comprises a connector for an external sample system.

8. The microfluidic cartridge of claim 7 wherein the connector is a Luer connector.

9. The microfluidic cartridge according to claim 1, characterized in that, in the cartridge, a microchannel system is developed that extends from a pump device through the detection chamber and a reaction chamber to a connector for the external sample system.

10. The microfluidic cartridge of claim 1 wherein the cartridge is formed from polycarbonate.

11. The microfluidic cartridge of claim 1 comprising a reaction chamber in fluid communication with the detection chamber wherein the reaction chamber comprises PCR chemicals protected by a wax layer.

12. The microfluidic cartridge of claim 11 further comprising a reservoir in fluid communication with the reaction chamber wherein the reservoir comprises lysing chemicals.

13. The microfluidic cartridge of claim 1 wherein the contact area comprises the contact pads disposed on a surface of the CMOS-based microchip.

14. The microfluidic cartridge of claim 1 wherein an electrical connection between each test site and the processing circuit consists essentially of the sigma-delta modulator.

15. A microfluidic cartridge for detecting biomolecules in a sample solution, having
  a detection chamber to which the sample solution is suppliable through a feed channel, and from which the analyzed sample solution is drainable through an outlet channel,
  a CMOS-based microchip that comprises a sensor area arranged in the detection chamber and a contact area that is fluid-tightly separated from the detection chamber,
  the sensor area of the microchip including an array of functionalized test sites for electrochemically detecting biomolecules in the sample solution, and
  each test site in the sensor area being furnished with its own sigma-delta modulator for the analog-to-digital conversion of electrical signals produced at the test sites upon electrochemical detection;
  wherein the cartridge comprises an integrated pump device that is in fluid communication with a reaction chamber and the detection chamber and that is configured to transfer the sample solution to the reaction chamber and from there in defined sample solution volumes to the detection chamber; and
characterized in that the pump device is developed as a double syringe for supplying a process fluid to a microchannel system in the cartridge, the double syringe comprising:
  a cylindrical outer chamber that defines a reservoir for receiving process fluid,
  arranged within the outer chamber, a cylindrical inner chamber that comprises, in its distal cylinder base surface, an outlet opening for connecting with the microchannel system in the cartridge, and that is in fluid communication with the outer chamber via through holes,
  an inner piston that is axially movable in the inner chamber and that, in a closed position, closes the through holes on the inner chamber side, and in a release position, releases the through holes and enables a fluid flow from the outer chamber to the inner chamber, and
  an annular piston that in the outer chamber is axially movable toward the distal end of the outer chamber,
  i) that, in a proximal reservoir position, closes off the reservoir for the process fluid,
  ii) through whose movement toward the distal end the process fluid provided in the reservoir is pushed via the through holes into the inner chamber when the inner piston is in its release position, and
  iii) that, in a distal closed position, closes the through holes from the outer chamber side and, in this way, enables fluid to be drawn back from the microchannel system in the cartridge into the inner chamber by axially moving the inner piston toward the proximal end.

* * * * *